(12) United States Patent
Pratt et al.

(10) Patent No.: US 9,107,720 B2
(45) Date of Patent: Aug. 18, 2015

(54) SURGICAL CABLE TENSIONING SYSTEM

(71) Applicant: Kinamed, Inc., Camarillo, CA (US)

(72) Inventors: William Ralph Pratt, Newbury Park, CA (US); Robert Bruce, Ventura, CA (US); Stephen F Howard, Nashville, TN (US); Vineet Kumar Sarin, Moorpark, CA (US); Clyde Ronald Pratt, Somis, CA (US); Richard L Kendall, Oak View, CA (US)

(73) Assignee: Kinamed, Inc., Camarillo, CA (US)

( * ) Notice: Subject to any disclaimer, the term of this patent is extended or adjusted under 35 U.S.C. 154(b) by 318 days.

(21) Appl. No.: 13/925,388

(22) Filed: Jun. 24, 2013

(65) Prior Publication Data
US 2014/0155906 A1 Jun. 5, 2014

Related U.S. Application Data

(63) Continuation-in-part of application No. 12/792,502, filed on Jun. 2, 2010, now Pat. No. 8,469,967.

(60) Provisional application No. 61/183,500, filed on Jun. 2, 2009.

(51) Int. Cl.
*A61B 17/88* (2006.01)
*A61B 17/84* (2006.01)

(52) U.S. Cl.
CPC .......... *A61B 17/8869* (2013.01); *A61B 17/842* (2013.01)

(58) Field of Classification Search
CPC .................................................... A61B 17/8869
See application file for complete search history.

(56) References Cited

U.S. PATENT DOCUMENTS 6,752,810 B1 * 6/2004 Gao et al. ...................... 606/103
2012/0197256 A1 * 8/2012 Knueppel ...................... 606/74

* cited by examiner

*Primary Examiner* — David Bates
(74) *Attorney, Agent, or Firm* — Koppel, Patrick, Heybl & Philpott

(57) ABSTRACT

A cable tensioning system includes a reaction frame which contains a sliding platform arranged to move linearly within the frame, and a clam-type cleat attached to the sliding platform. The cleat features one or more grooves, each of which comprises two arrays of opposing ridges that converge to form a V-shape groove adapted to receive a length of cable. The ridges of each groove are tilted relative to an axis perpendicular to the groove's longitudinal axis, such that the cable is progressively captured between the ridges of the opposing arrays as it settles into the crotch of the groove when moved in a first direction, and can be disengaged from the cleat by relaxing the axial force on the cable and moving it in the opposite direction. A linear actuator mechanism may be coupled to the sliding platform to move the platform with respect to the reaction frame.

25 Claims, 13 Drawing Sheets

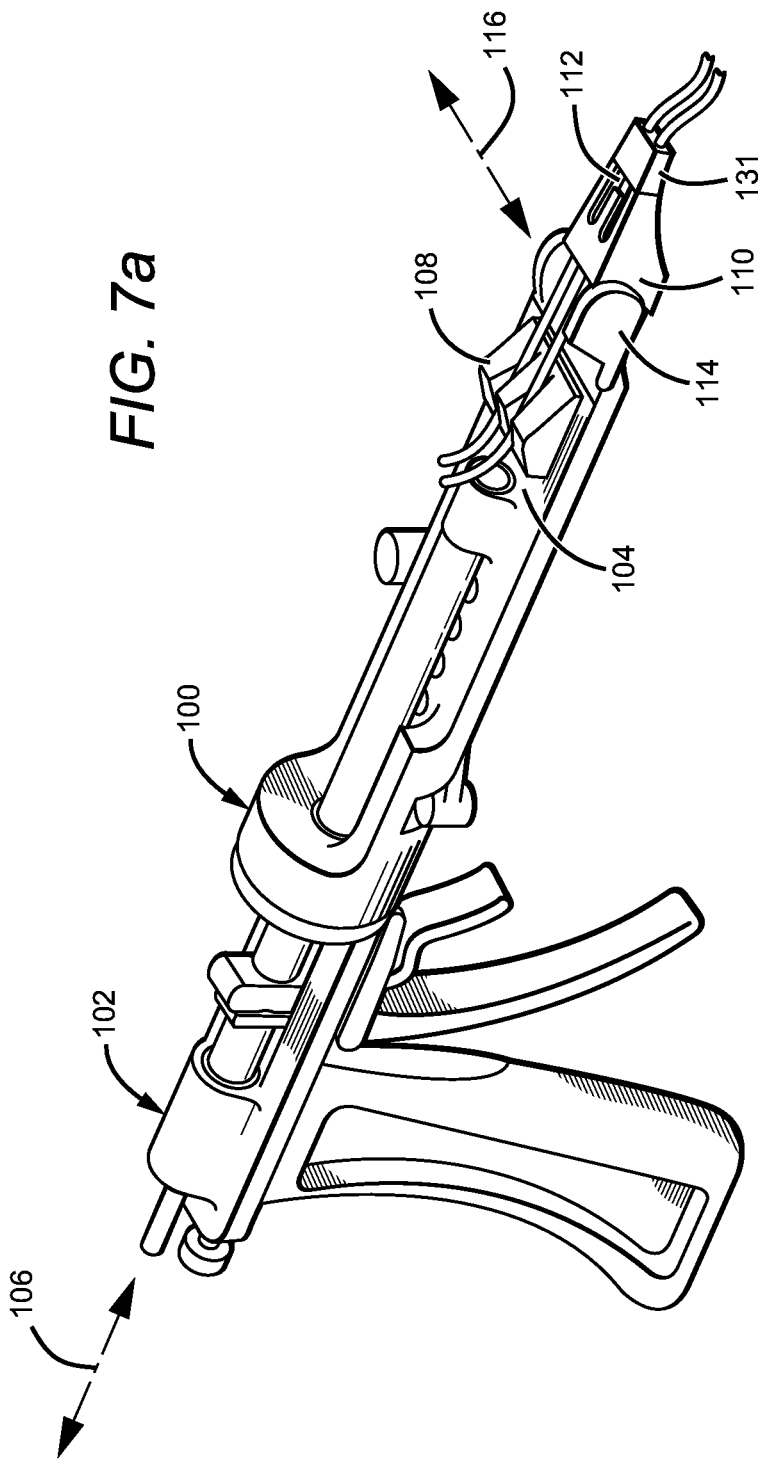

FIG. 10b
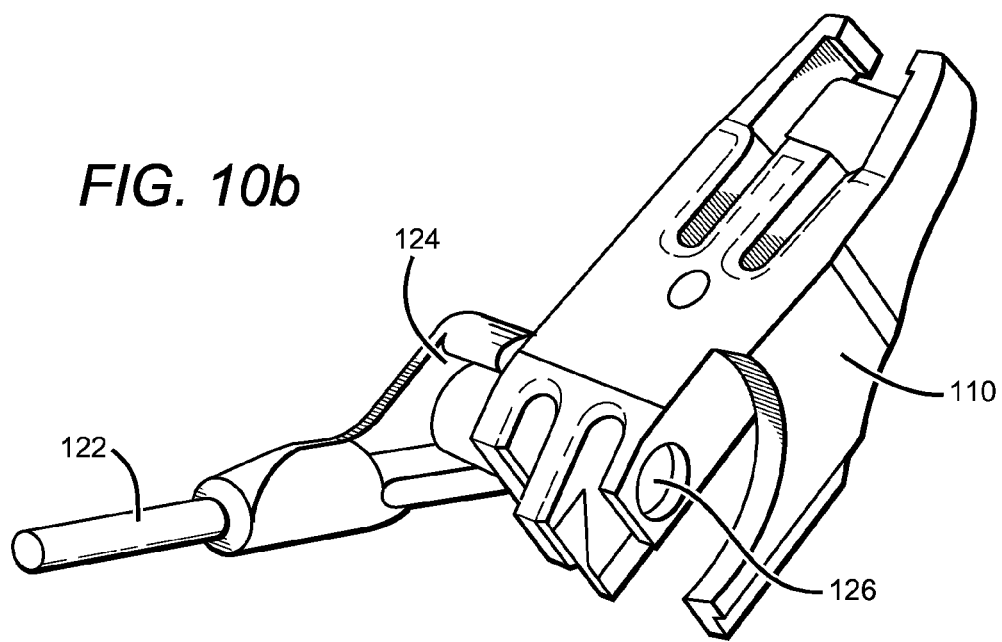
FIG. 10c
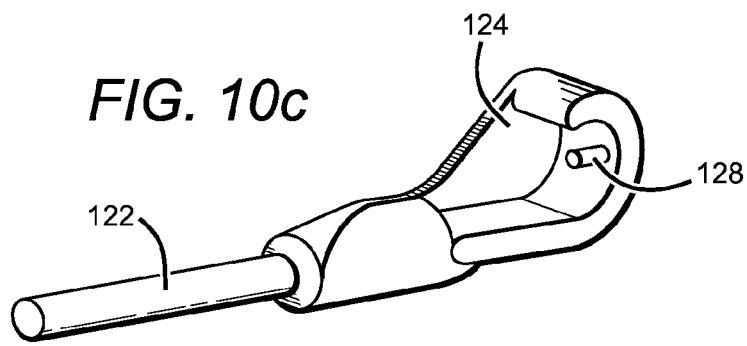
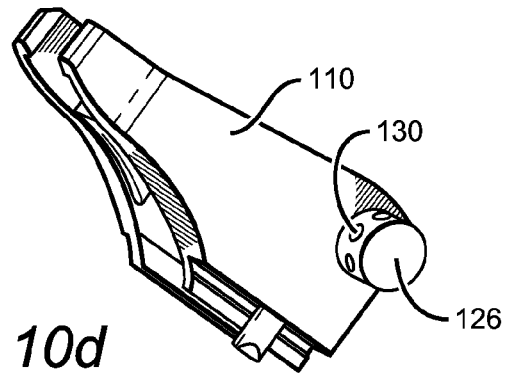
FIG. 10d

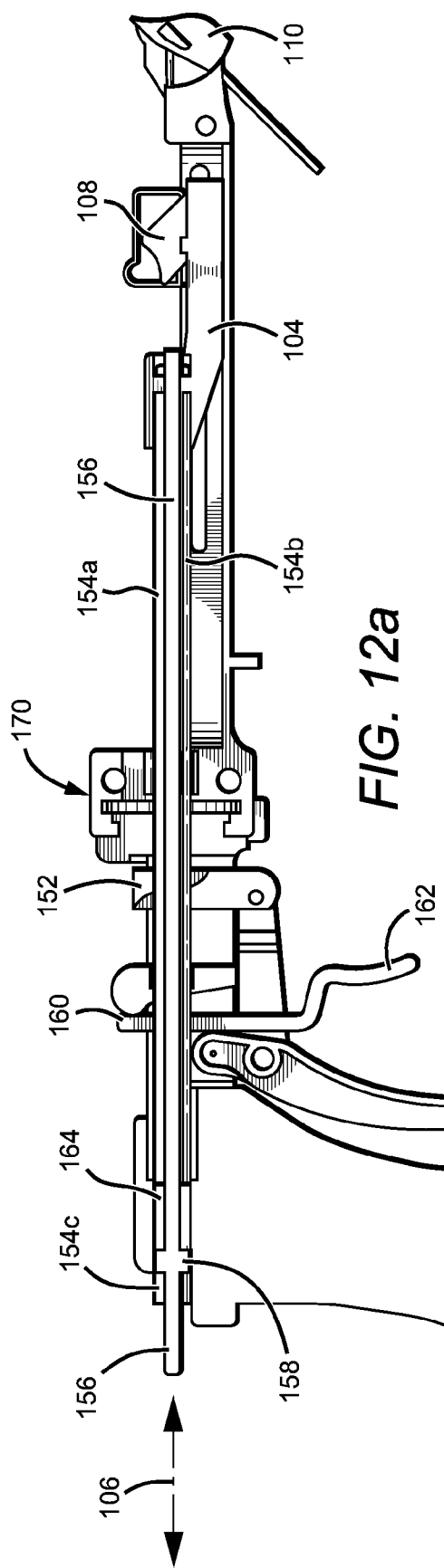
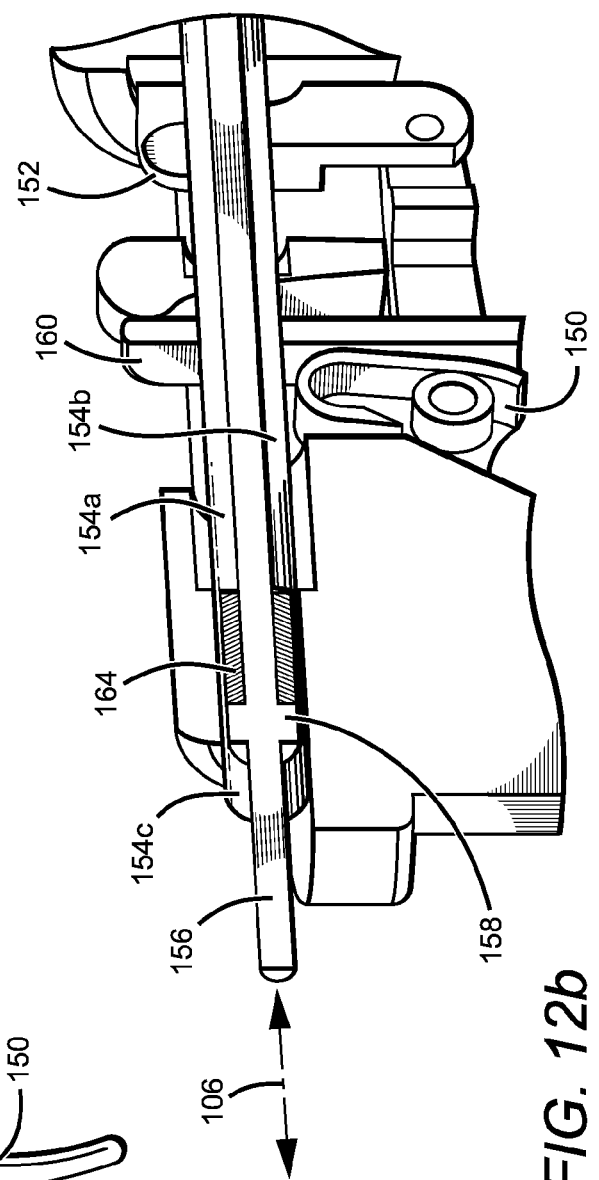
FIG. 12a
FIG. 12b

SURGICAL CABLE TENSIONING SYSTEM

RELATED APPLICATIONS

This application is a Continuation-in-Part of U.S. utility application Ser. No. 12/792,502, filed Jun. 2, 2010, still pending, which claimed the benefit of provisional patent application No. 61/183,500, filed in the U.S. Patent and Trademark Office on Jun. 2, 2009.

BACKGROUND OF THE INVENTION

1. Field of the Invention

This invention relates generally to cable tensioning systems, and more particularly to systems for tensioning surgical cables employed to hold human body tissues and/or bones in a desired relationship or position.

2. Description of the Related Art

Many products are known which serve to hold human body tissues and bones in a desired relationship or position, to aid in their healing when injured or diseased. One such product is the surgical cable, which can be wrapped around the fragments of a fractured bone, for example, such that a compressive force is applied which aids in the healing of the bone. Such a cable is described, for example, in U.S. Pat. No. 6,589,246 to Hack et al.

After the cable has been wrapped around the anatomical structures to be held, the resulting looped cable is tightened to apply a desired level of compressive force to the structures. The cable forming the loop is then locked into place with a cable retaining device such as that described in U.S. Pat. No. 7,207,090 to Mattchen.

Tightening the looped cable to apply a desired level of compressive force requires a means of tensioning the cable. Previous systems have used various types of actuated clamping jaws to grip the cables. For example, one such tensioning system, described in SuperCable™ Iso-Elastic™ Cerclage System—Surgical Technique, Kinamed Inc. (2008), employs a clamping jaw that is screwed down using a hand operated wrench. However, the swing of the wrench requires unrestricted space that may not be available when working in deep wounds; i.e., the patient's muscle and fatty tissues may crowd in around where the tensioner needs to be deployed. Such systems may also be seen as suboptimal in terms of reliability and time required to operate.

SUMMARY OF THE INVENTION

A cable tensioning system is presented which provides a simple, convenient, and reliable means of tensioning a cable, and is particularly well-suited for use in tensioning surgical cables which have been wrapped around one or more tissues and/or bones.

In one embodiment, the present tensioning system includes a reaction frame which contains a sliding platform arranged to move linearly within the frame along a first axis, and a clam-type cleat attached to the sliding platform. The cleat features one or more grooves, each of which comprises two arrays of opposing ridges that converge to form a V-shape. Each of the V-shaped grooves has a longitudinal axis which is approximately parallel to the first axis, and is adapted to receive a length of cable such that the cable lies along an axis approximately parallel to the groove's longitudinal axis. The ridges of each groove are tilted relative to an axis perpendicular to the groove's longitudinal axis, such that the length of cable is progressively captured between the ridges of the opposing arrays as it settles into the crotch of the groove when moved in a first direction relative to the cleat, and such that the cable can be disengaged from the cleat by relaxing the axial force on the cable and moving it in the opposite direction.

A linear actuator mechanism is preferably coupled to the sliding platform and arranged to move the sliding platform with respect to the reaction frame; the mechanism can be arranged to be driven by either manual or powered means. The system may also include an anti-snag device arranged to occlude the grooves and thereby prevent the cable from being captured if desired. A threading assist device (TAD) may be coupled to the reaction frame to assist in threading cables to be tensioned into the tensioning system.

In another embodiment, the TAD includes a wrist joint such that the distal end of the TAD can pivot up and down around a wrist joint axis which is perpendicular to the first axis. The tensioning system may also include a linear tension mechanism coupled to the sliding platform and arranged to pull the sliding platform toward the proximal end of the reaction frame when actuated. In one embodiment, the linear tension mechanism is in the form of a rotatable hand-operated lever which is coupled to the sliding platform via a non-toothed ratchet mechanism. A set-bar mechanism may also be included which engages with a cable retaining device through which one or more surgical cables is threaded en route to the TAD, and is arranged to cause the cable retaining device to lock the cables in place when the set-bar mechanism is actuated.

These and other features, aspects, and advantages of the present invention will become better understood with reference to the following drawings, description, and claims.

BRIEF DESCRIPTION OF THE DRAWINGS

FIGS. 7a and 7b are perspective views of another possible embodiment of the present surgical cable tensioning system.

FIGS. 10a-10d are isolated and cutaway views of an angle lock mechanism as might be used with a TAD such as that shown in FIG. 8.

FIGS. 12a and 12b are isolated and cutaway views illustrating a linear tension mechanism as might be used with the present surgical cable tensioning system.

DETAILED DESCRIPTION OF THE INVENTION

A cable tensioning system in accordance with the present invention provides a simple, convenient, and reliable means of tensioning a cable. A primary application of the system is to apply tension to a surgical cable or cables which have been wrapped around one or more tissues and/or bones, such that the cables apply a compressive force to the tissues to aid their healing.

Figure 1A:
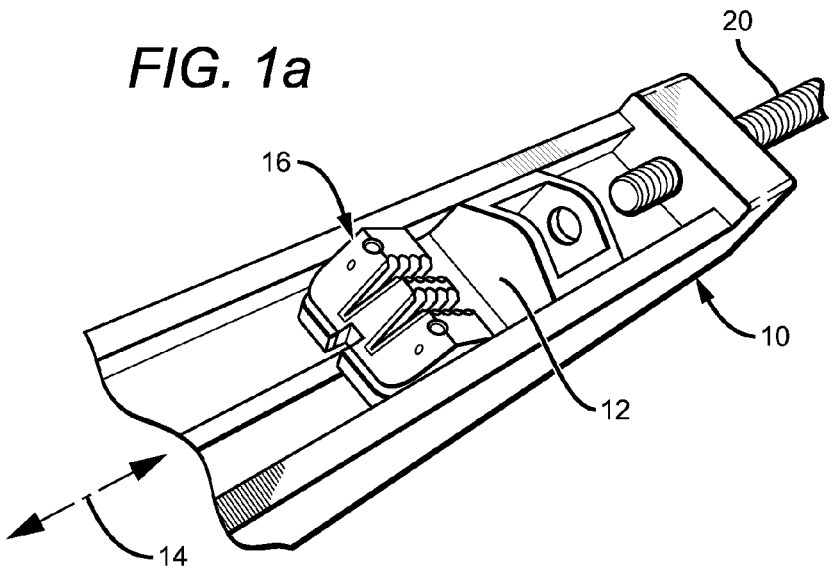
FIGS. 1a and 1b are perspective views of one possible embodiment of a surgical cable tensioning system in accordance with the present invention.
Figure 1B:
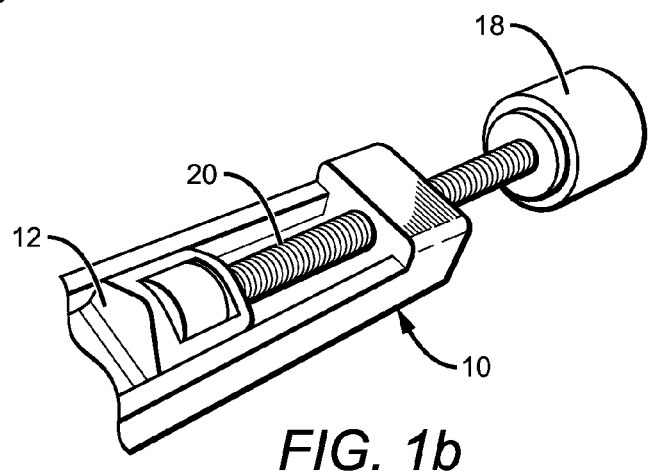

FIGS. 1a and 1b show one possible embodiment of a surgical cable tensioning system in accordance with the present invention. The system includes a reaction frame 10 which supports a sliding platform 12 which is arranged to move linearly within the frame along a first axis 14; sliding platform 12 might include rollers which track corresponding slots in the inner sidewalls of reaction frame 10 to facilitate sliding. The system also includes a clam-type cleat 16 (not visible in FIG. 1b) attached to sliding platform 12 such that it moves linearly within frame 10 along with the platform.

The system preferably also includes a linear actuator mechanism 20 which is coupled to sliding platform 12 and is arranged to move the sliding platform linearly with respect to reaction frame 10 when actuated. The linear actuator mechanism may be driven by manual or powered means. The driving means may have, for example, a rack configuration, or a screw configuration as shown in FIGS. 1a and 1b, which moves sliding platform 12 with respect to reaction frame 10 when rotated. A screw configuration may utilize a multiple-start threaded screw that results in faster actuation of the sliding platform. When a screw configuration is employed, linear actuator mechanism 20 may include a tightening knob 18 attached to the screw. The tightening knob might include a torsion spring coupled to the screw, arranged such that turning the knob deflects the spring and adjusts the tension realized in the cable. Preferably, the amount of tension realized in the cable for a given amount of deflection in the torsion spring is known.

Figure 2A:
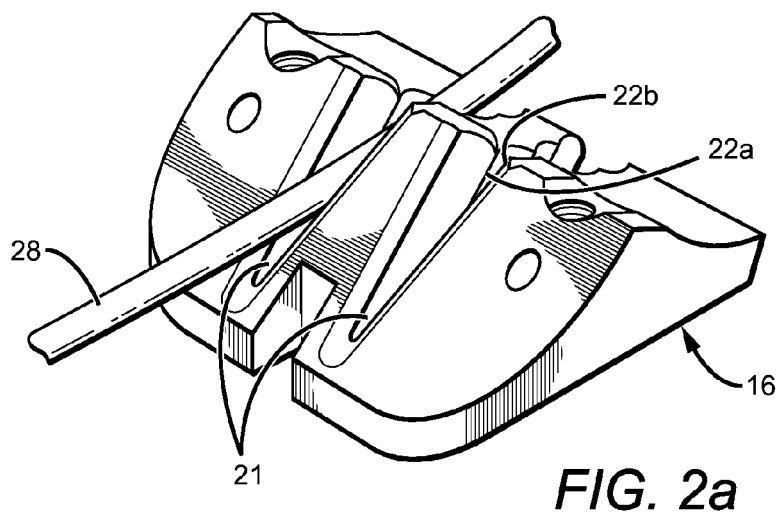
FIGS. 2a and 2b are perspective views of the clam-type cleat used with the present surgical cable tensioning system.
Figure 2B:
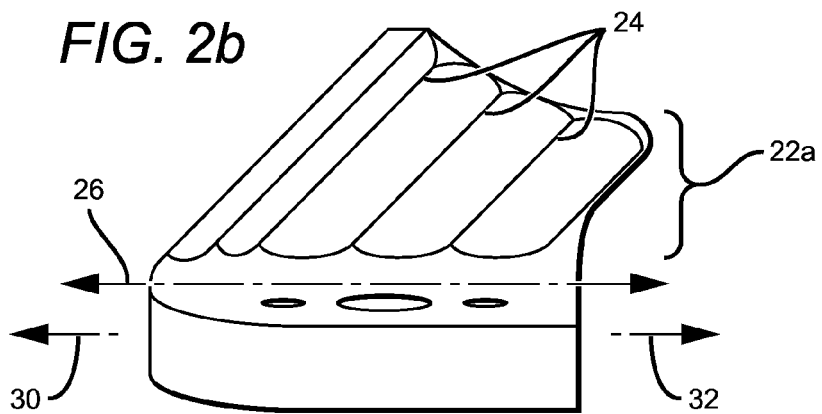

Cleat 16 is a clam-style cleat; such cleats have no moving parts and are often used in nautical applications, typically anchored in a static position, to temporarily grasp woven ropes and cables. Clam-type cleats are well-known and available from many manufacturers, such as Clamcleats Limited in Welwyn Garden City, England. As shown in FIGS. 2a (perspective view) and 2b (cutaway view), the cleat has one or more grooves 21 (two grooves are shown in FIG. 2a; one-half of one groove is shown in FIG. 2b). Each groove comprises two arrays 22a, 22b of opposing ridges 24 that converge to form a V-shape. Each of the V-shaped grooves has a longitudinal axis 26 which, when mounted to sliding platform 12, is approximately parallel to first axis 14. Each groove is adapted to receive a length of cable 28 such that, when positioned in the groove, the length of cable lies along an axis approximately parallel to the groove's longitudinal axis 26.

The opposing ridges of each groove are tilted relative to an axis perpendicular to the groove's longitudinal axis, such that the cable 28 is progressively captured between the ridges of the opposing arrays as it settles into the crotch of the groove when moved in a first direction 30 relative to the cleat 16. The cable is ultimately directed to an intense pinch point, at which the cable can resist great axial force without slipping within the cleat and without breakage or fracture of the cable. The cable is disengaged from the cleat by relaxing the axial force on the cable and moving the cable in the direction opposite the first direction (32), because in that direction the ridges are diverging and the cable is immediately directed away from the pinch point. The number and configuration of the ridges are important in consideration of the surgical cable tensioning system, because the pinching effect must be controlled and shared in several locations along the cable in order to develop the desired tensile load without slippage or breakage. The cleat can be made from almost anything rigid, but metal, high performance plastic, or ceramic would be the most likely candidates for surgical use. In a preferred embodiment, the clam-type cleat has two V-shaped grooves as described above, and is designed to receive and capture polymer surgical cable.

Although the cleat itself has no moving parts, the configuration of the ridges is critical to the success of the system, which is preferably designed specifically for use with an intended cable-type such as polymer surgical cable. The phenomenon of convergence leading to an effective, yet not-overwhelming, pinch point is controlled by a concert of shapes acting in proportion to the size and composition of the cable. The groove's V-shape naturally accommodates a range of cable diameters without adjustment, with the range governed by the width of the opening at the top of the "V", and how narrow it gets at the bottom of the "V". A cleat which provides an adjustable "V"—with sides that could be moved apart or closer together to extend the range—is also contemplated.

One advantage of the present system is its ability to easily engage a cable at the site of a surgical wound, due to the V-shaped grooves of the clam-type cleat. This is important because of the elasticity of the typical surgical cable, and the need to apply load to the smallest initial cable length possible. The V-shaped grooves eliminate the need to tighten a holding mechanism as with previous designs; here, the cable is simply depressed into the grooves. Note that V-shaped grooves as described herein reliably engage the cable even when slippery due to the patient's bodily fluids and/or fat.

To make the "V" an easy visual target for engaging the cable, each leg or side of the "V" is preferably in two segments. Near the top or opening of the "V", the angle of the "V" is wider. The angle between the sides, however, preferably changes and narrows closer to the point of the "V", a feature that is critical for creating mechanical advantage in the pinching process. Too broad an angle at the point of the "V" will defeat the pinching action, so it should be under 25 degrees inclusive. The sides should not actually touch or completely converge at the point of the "V", however, because this could cut the cable or fracture its core. In other words, the pinching process should be halted at a certain point of engagement. On the other hand, if the sides are too far apart, the pinch will be insufficient to resist the high axial load that needs to be imparted to the cable for its installation without the cable slipping through the cleat. The compound angle in the "V" also allows the "V" to be shorter in height for a given amount of desired opening, thus making the overall cleat more compact. The ridges themselves must not be so sharp as to slice the cable, but still must be able to bluntly dig into it. The number of ridges on each side of the "V" may vary from one to many, but one ridge is likely to overload one location on the cable when high axial force is applied, and over four ridges is potentially redundant and lessens the compactness of the device.

The angle at which the ridges are tilted relative to the axis of the cable affects the mechanical efficiency of the pinch process, compactness of the device, and the ease with which the cable is removed from cleat. If the ridges are perpendicular to the longitudinal axis of the groove, there is little natural tendency for the cable to be directed down into the pinch point. If the ridges are tilted almost all the way over, then the groove must necessarily become stretched out and take up more room. Having the ridges tilted to an angle of 45±20 degrees with respect to the perpendicular is preferred.

In practice, once a cable which is wrapped around some tissues has been sufficiently tensioned by the present system, the cable is locked into place and the tensioning system removed. An "anti-snag" device may be employed to prevent the cables from inadvertently re-engaging with the cleat when removing the tensioning system. Such a device operates by occluding the grooves of the cleat.

Figure 3:
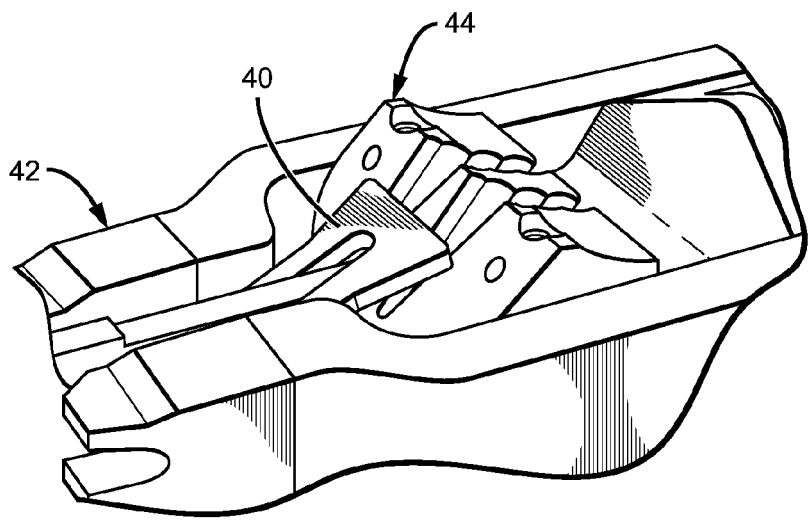
FIG. 3 is a perspective view of one possible embodiment of an anti-snag device as might be used with the present surgical cable tensioning system.

One possible anti-snag device, shown in FIG. 3, comprises a flap 40 connected to the reaction frame 42 and arranged to automatically ride up the face of the cleat 44 and occlude its grooves when the cleat is at a predetermined position with respect to the frame. Typically, flap 40 would be mounted at the end of the reaction frame nearest the point of engagement with the cable, such that the flap rides up the face of the cleat and occludes the grooves when the sliding platform is advanced completely to that end of the reaction frame.

Figure 4A:
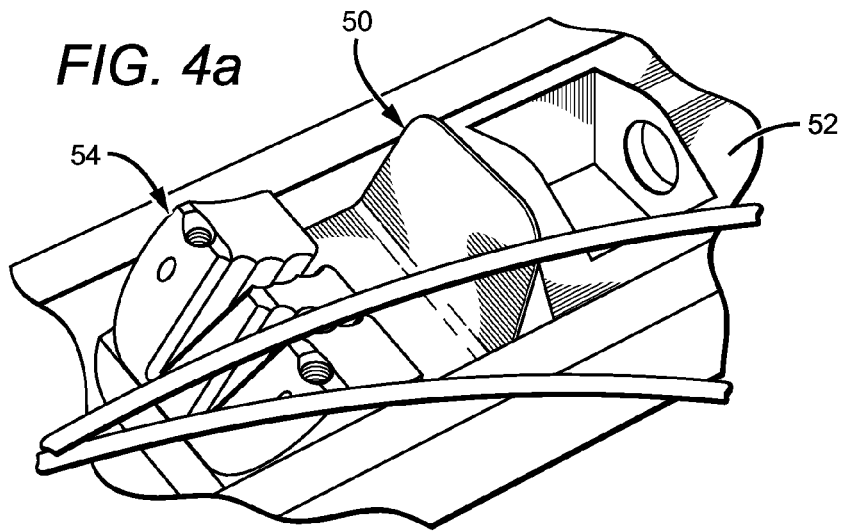
FIGS. 4a and 4b are perspective views of another embodiment of an anti-snag device as might be used with the present surgical cable tensioning system.
Figure 4B:
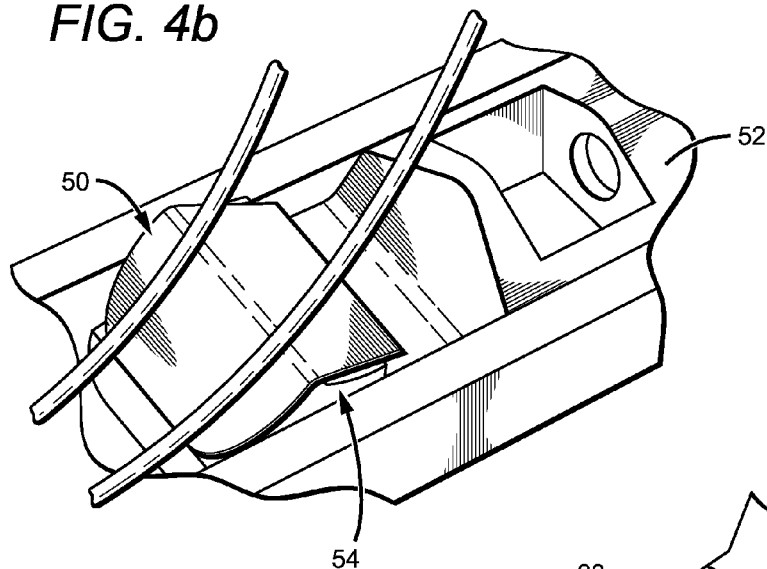

Another possible anti-snag device, which can be manually deployed to occlude the cleat grooves, is illustrated in FIGS. 4a and 4b. Here, the anti-snag device takes the form of a shield 50 which is attached to the sliding platform 52, and can be manually rotated such that the grooves of cleat 54 are unaffected (FIG. 4a) or occluded (FIG. 4b) as needed.

The advantages of using an anti-snag device are important for surgical convenience. The clam-type cleat employed in the present system is highly effective at grasping the cable, and the slightest engagement with the cable is quickly amplified when the cable is pulled relative to the cleat in the direction of convergence. After the cable has been tensioned and locked, there is a natural tendency of the cable to snag in the cleat as the tensioner is pulled away from the installation site, because that motion is again moving the cable in the direction of convergence.

Figure 5A:
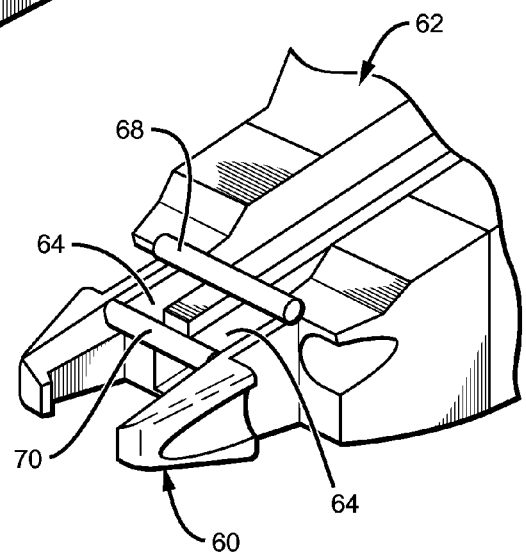
FIGS. 5a-5c are perspective views of a threading assist device as might be used with the present surgical cable tensioning system.
Figure 5B:
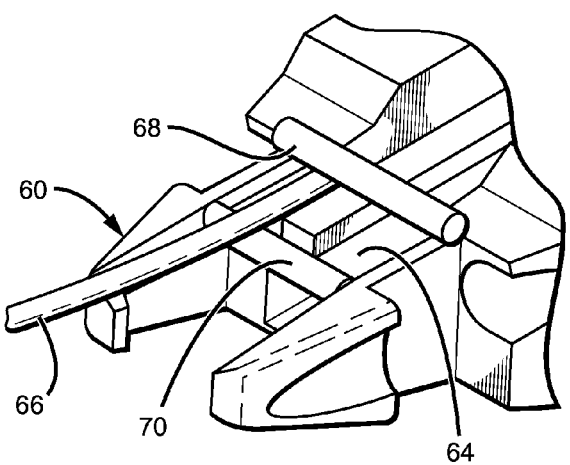
Figure 5C:
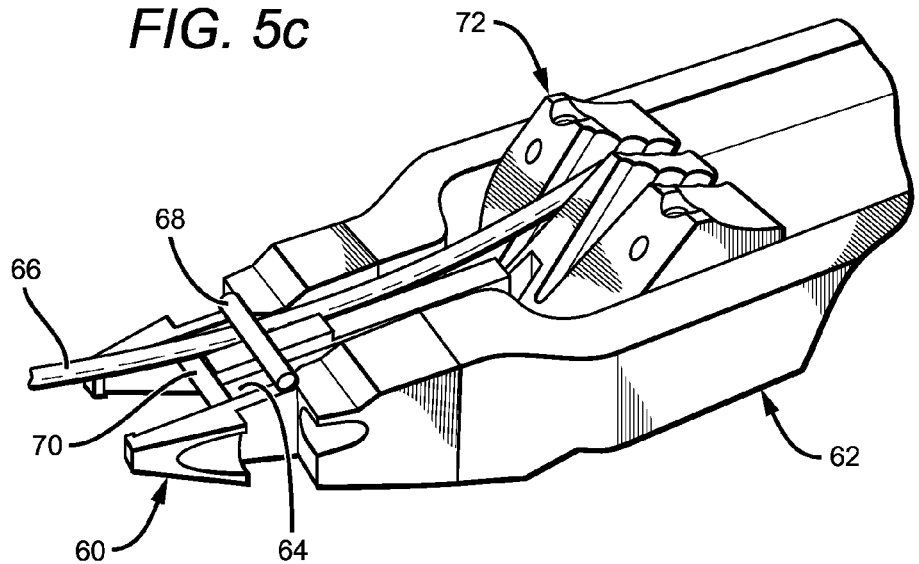

The present tensioning system may also include a threading assist device, to assist in threading the cable or cables into the cleat; one possible threading assist device is illustrated in FIGS. 5a-5c. The threading assist device 60 is coupled to the reaction frame 62, and includes at least one channel 64 (two channels are shown in FIGS. 5a-5c), each channel oriented such that its longitudinal axis is approximately parallel to first axis 14 and adapted to receive a length of cable 66. The threading assist device preferably also includes upper and lower bars 68, 70 which span the channels so as to, in concert with the sidewalls of the channels, form at least one closed loop through which a length of cable to be tensioned is threaded en route to the grooves of the cleat 72; one closed loop is formed for each channel spanned by bars 68 and 70. The upper and lower bars are preferably staggered along the channels' longitudinal axes so as to increase the effective size of the closed loops and thereby increase the ease with which the necessary threading step may be completed. As best seen in FIG. 5c, the channels 64 serve to direct the cables into the grooves of the cleat 72.

Figure 6:
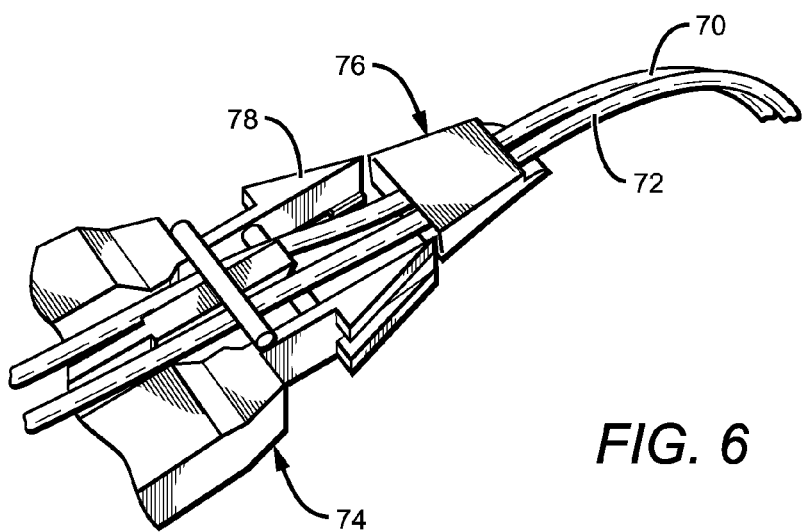
FIG. 6 is a perspective view of one possible embodiment of the present surgical cable tensioning system and a cable retaining device as they might be employed in practice.

Once the cable has been tensioned as needed, its free ends may be secured with, for example, a cable retaining or locking device through which the cable is threaded and which can be operated so as to inhibit movement of the cable with respect to the retaining device. One such possible arrangement is shown in FIG. 6, which shows cables 70 and 72 threaded through threading assist device 74 (the cleat, reaction frame and sliding platform are not shown) and a cable retaining device 76. One suitable cable retaining device is described in U.S. Pat. No. 7,207,090 to Mattchen.

The threading assist and cable retaining devices may include mating features which control the alignment and transfer of forces between the two devices when they are in contact with each other. For example, the "nosepiece" 78 of the threading assist device may have a pair of "L"-shaped projections at its tip that loosely embrace a pair of corresponding notches in the retaining device 76, with the "feet" of the "L"s butting against the opposing sides of the notches as tension is applied. In actual use, the cable is first threaded through the cable retaining device and then into the present tensioning system. Tension is then applied as needed, the retaining device is locked with a locking device such as a wedge, and the tensioning system is removed. The mating features enable an alignment between the devices which facilitates the efficient development of high tension, as well as the operation of the push rod mechanism for setting the locking wedge into place within the retaining device. The mating features are preferably arranged such that, as tension is applied, the notches guide the locking device to a pair of stops built into the "L"s.

The threading assist device is preferably configured to guide the tensioner along the cable in a sliding manner to the target mating position with the cable retaining device. Note that if the staggered bars 68, 70 are positioned too close to the tip of nosepiece 78, then the cable may be too constrained and can interfere with the nosepiece's ability to mate with the cable retaining device. Alternatively, if the bars are positioned too far away from the tip of the nosepiece, then there may not be enough constraint, such that the tip may be allowed to wander off target and fail to conveniently mate with the retaining device. The ability to easily mate with the retaining device is especially important in deep wounds were visualization is a challenge.

The present tensioning system provides a number of advantages over previous systems. For example, no moving parts are required to provide the gripping function, thus lowering production cost, improving sanitization after surgery, improving reliability and durability, and reducing the working space required to operate the tensioning system, thereby enabling the system to be more easily used in deep wounds. The time required to operate the screw as found in previous designs is eliminated in the present system, thus reducing the length of time required for surgery and providing an immediate health benefit to the patient and cost benefit to the hospital. Furthermore, since polymer cables are elastic and the cleat can be positioned closer to the engagement end of the reaction frame (i.e. deeper in the wound) because of the reduced working space requirement, the length of cable needing to be stretched is reduced and less motion is required to fully tension it—so operative time is again reduced. These time savings are multiplied in complex surgeries wherein multiple cables are used, thereby saving several minutes of costly operating room time per surgery.

As noted above, the linear actuator may utilize a multiple-start threaded screw that results in faster actuation of the sliding platform. A multiple-start threaded actuator reduces the time required to actually stretch and therefore tension the cable, and thus is well-suited for use with a flap-style anti-snag device shown in FIG. 3, because it enables the sliding platform to be moved towards the flap more quickly for a given amount of effort than is possible with previous devices.

Polymer surgical cables are frequently composed of materials having a remarkably low coefficient of friction such as polyethylene, thus it is a challenge to grasp them sufficiently for imparting tensile forces in excess of 100 lbs. (~445N) as is required for surgical efficacy. The passive design of the present system is especially effective at reliably grasping such cables for such purposes. Testing in a simulated use environment, including simulation of lubricious physiological fluid contact, demonstrated that the present tensioning system is able to impart at least 900 Newtons of tensile load to a polymer surgical cable that is coated with physiological lubricant.

Figure 7B:
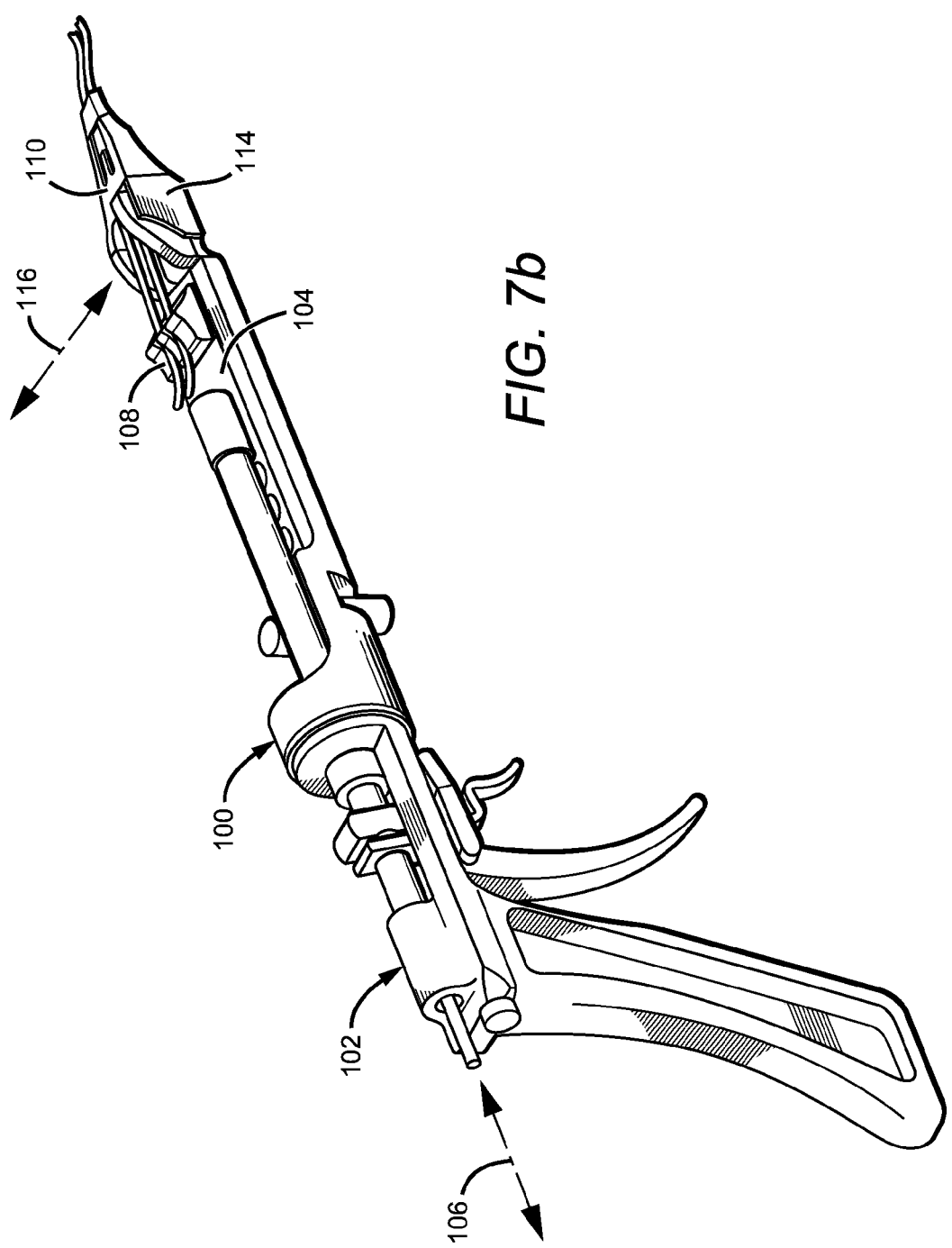

Another possible embodiment of the present tensioning system is shown in FIGS. 7a and 7b. This embodiment includes a reaction frame, preferably comprising a forward section 100 and a rear section 102, and a sliding platform 104 within the reaction frame which is arranged to move linearly within the frame along a first axis 106. A clam-type cleat 108 as described above is attached to sliding platform 104.

Figure 8:
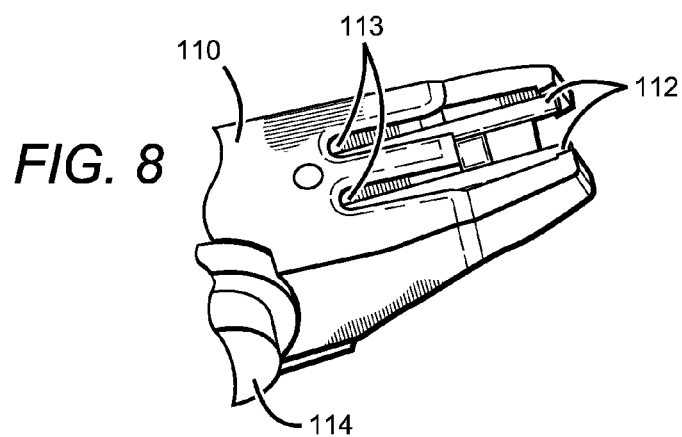
FIG. 8 is a perspective view of a threading assist device (TAD) as might be used with the present surgical cable tensioning system.
Figure 9A:
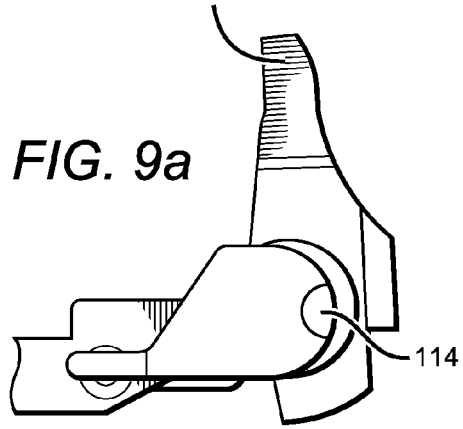
FIGS. 9a and 9b are elevation views illustrating the range of motion possible with a TAD such as that shown in FIG. 8.
Figure 9B:
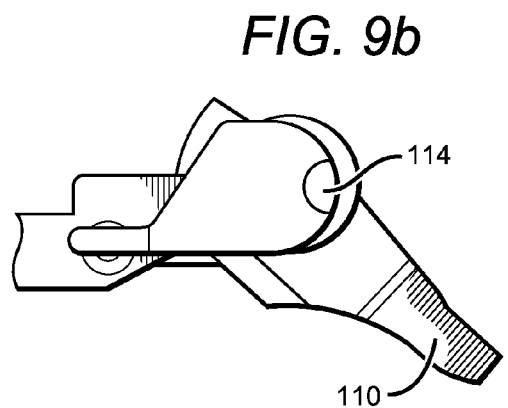
Figure 10A:
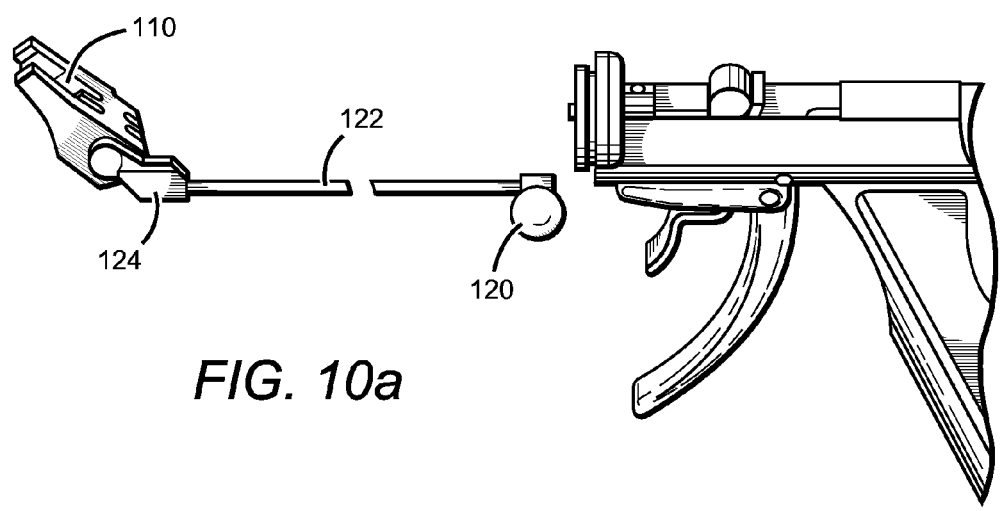

The embodiment includes a threading assist device (TAD) 110 (shown in close-up in FIG. 8), which includes at least one channel adapted to receive a length of cable (two are shown in the illustrated example), each channel having an open slot portion 112 and a closed tunnel portion 113 which lie along a longitudinal axis which is approximately parallel to the first axis. The TAD includes a wrist joint 114 which couples the TAD to the distal end of the reaction frame such that the TAD can pivot up and down around a wrist joint axis 116 which is perpendicular to the first axis (illustrated in FIGS. 9a and 9b). The system may be arranged such that the TAD has a range of motion from +90° to −60° with respect to the first axis, with a minimum range of +60° to −45° preferred.

As shown in the isolated and cutaway views in FIGS. 10a-10d, the present embodiment also preferably includes an angle lock mechanism, to enable a user to lock the TAD at one of a plurality of predetermined angles with respect to the first axis. The angle lock mechanism preferably includes a finger button 120, located away from TAD 110, connected to a shaft 122 that runs towards the wrist joint and terminates in a small frame 124 that surrounds an axle 126 of the wrist joint. The frame has an engagement pin 128 that can index into cavities 130 in axle 126 at predetermined positions of rotation.

Figure 11A:
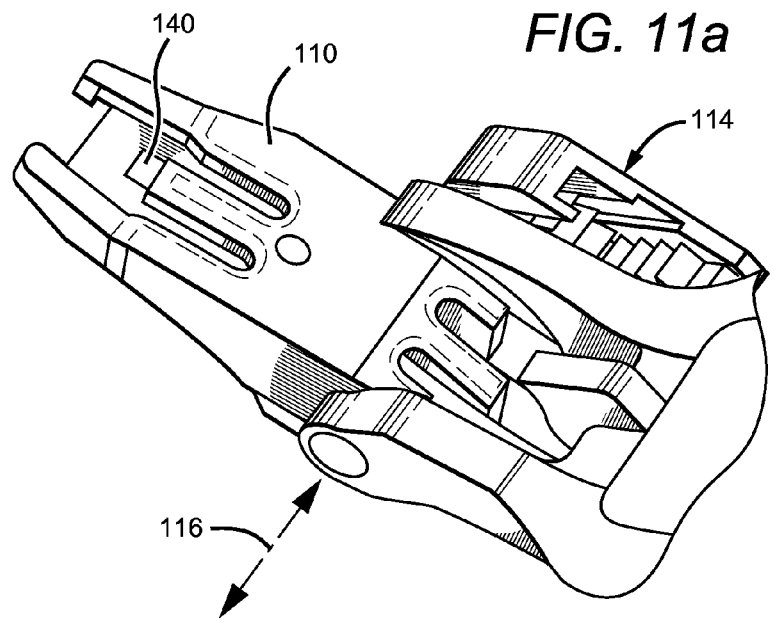
FIGS. 11a-11c are isolated and cutaway views of a set-bar mechanism as might be used with a TAD such as that shown in FIG. 8.

As noted above, surgical cables to be tensioned are typically routed through a cable retaining device; one such device 131 in shown in FIG. 7a (another, cable retaining device 76, was shown in FIG. 6). Once an appropriate amount of tension has been applied to the cables, a locking wedge (not shown) is forced into the proximal side of device 131 to secure the cables in place. This is preferably accomplished with a set-bar mechanism such as that illustrated in FIGS. 11a, 11b and 11c. The mechanism includes a linear actuator 140 within TAD 110 which engages the locking wedge and drives it into the cable retaining device when actuated. Linear actuator 140 is preferably actuated with a hand-operated lever 141 mounted to the reaction frame. A shaft 142 is connected between lever 141 and a coupling means 143. In operation, moving hand-operated lever 141 causes shaft 142 to move along an axis parallel to the first axis, causing coupling means 143 to actuate linear actuator 140.

Figure 11B:
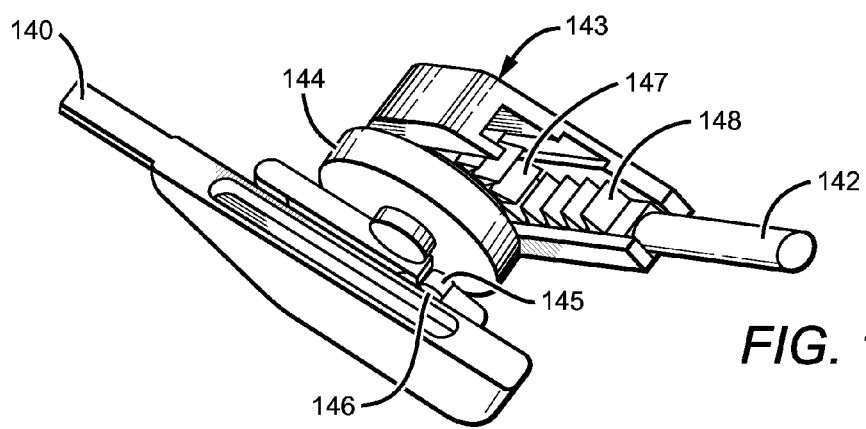
Figure 11C:
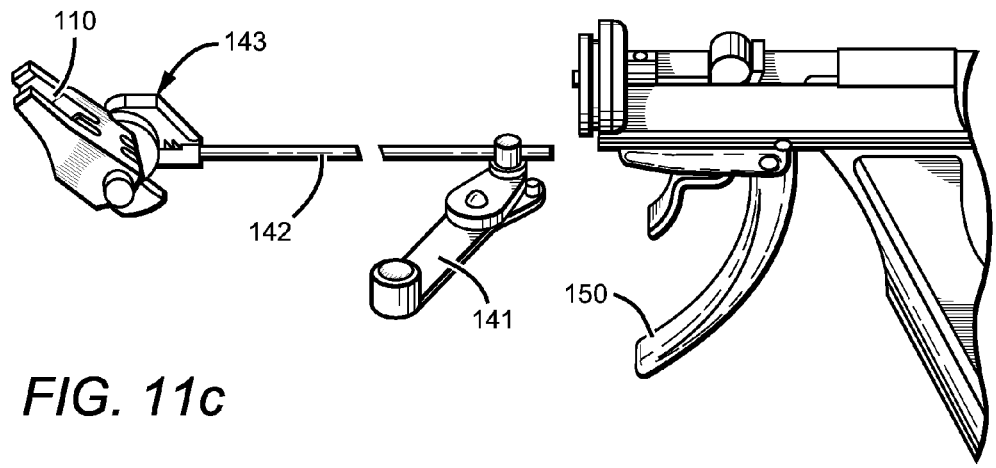

One way in which coupling means 143 might be implemented is illustrated in FIG. 11b. A wheel 144 turns about the axis 116 of the wrist joint, and on one side of the wheel near its perimeter there is a perpendicular boss 145 that engages a slot 146 in linear actuator 140 and propels the actuator forward as the wheel is rotated. On the other side of the wheel is a concentric and integrated pinion gear 147. Aligned to the pinion gear is a rack gear 148 which stands clear the pinion until it is moved in a linear manner, at which point the teeth in the rack gear mesh with the teeth in the pinion and drive the pinion and wheel about the axis of the wrist joint. Rack gear 148 is attached to shaft 142 that runs back to hand-operated lever 141. In this way, linear actuator 140 is powered through wrist joint 114, however it is rotated, without impinging the rotation.

As shown in FIGS. 12a and 12b, a linear tension mechanism is coupled to sliding platform 104 and arranged to pull sliding platform toward the proximal end of the reaction frame when actuated. The linear tension mechanism preferably includes a hand-operated lever 150 mounted to the rear section 102 of the reaction frame; a tensioning mechanism 152 is coupled between the hand-operated lever and sliding platform 104 such that the sliding platform is pulled toward the rear section of the reaction frame when the hand-operated lever is actuated.

The preferred linear tension mechanism also includes a rod (154a, 154b, 154c) having a longitudinal axis which is oriented parallel to first axis 106, which is moved along its longitudinal axis toward the proximal end of the reaction frame when hand-operated lever 150 is actuated. The rod has two bores (154a, 154b) running lengthwise, with a single larger bore (154c) at its proximal end. The rod is not attached directly to sliding platform 104. The mechanism also includes a drawbar 156 which is coupled to sliding platform 104 and freely runs through rod 154a, 154b, 154c; the drawbar preferably has a feature 158 which has a wider diameter than the rest of the drawbar, located in the larger bore portion (154c) of the rod.

Tensioning mechanism 152 is preferably a non-toothed ratchet mechanism coupled between hand-operated lever 150 and rod 154a, 154b, 154c, which causes the rod to move toward the proximal end of the reaction frame when the hand-operated lever is actuated. A keeper mechanism 160 which has 'normal' and 'release' states may be used, arranged to prevent the rod from moving back toward the distal end of the reaction frame when in its normal state and to allow the rod to move back toward the distal end when in its release state. Keeper mechanism 160 preferably includes a finger release 162 positioned within reach of a user's finger when the user's hand is on hand-operated lever 150; the keeper mechanism is arranged to transition from its normal state to its release state when the finger release is pulled.

A stack of spring washers 164 is preferably placed between the proximal end of rod 154a, 154b, 154c and the wider diameter portion 158 of drawbar 156. In operation, rod 154a, 154b, 154c is pulled back when hand-operated lever 150 is actuated, which in turn compresses springs 164 against the thicker part 158 of drawbar 156, which in turn pulls on the sliding platform 104 at the opposite end. As the springs compress, the rear end of drawbar 156 progressively extends out past the end of larger bore portion 154c as the force increases. The amount of extension is directly related to the tension in the cable. If the spring constant of the spring washers is known, they can be used as a "reference spring"; then, with calibrated graduated marks placed on the portion of the drawbar that extends out past bore 154c, a direct, visible tension force measurement can be provided to the user.

Figure 13A:
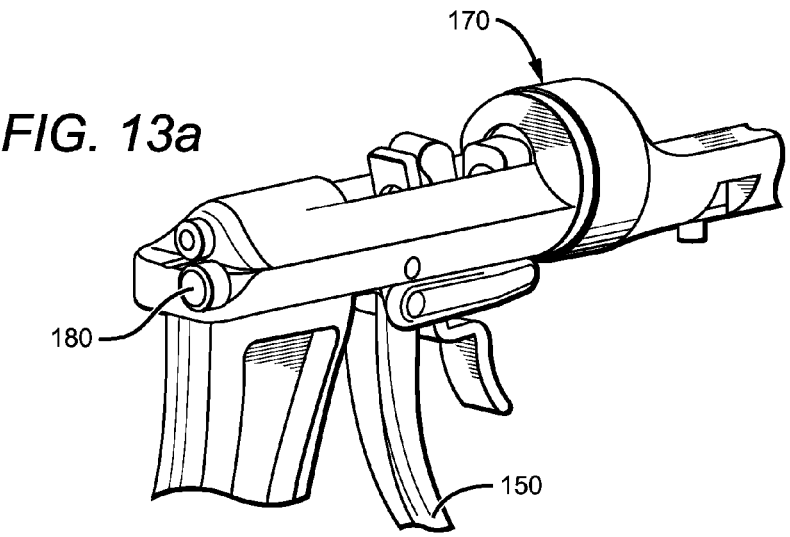
FIGS. 13a-13e are isolated and cutaway views of a rotation lock mechanism as might be used with a linear tension mechanism such as that shown in FIGS. 12a and 12b.
Figure 13B:
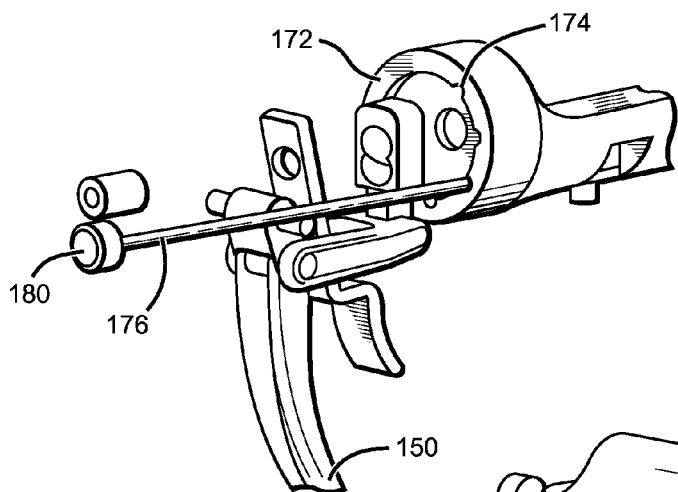
Figure 13C:
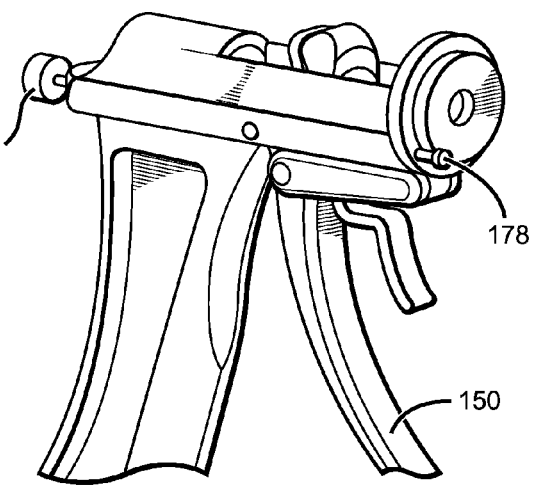
Figure 13D:
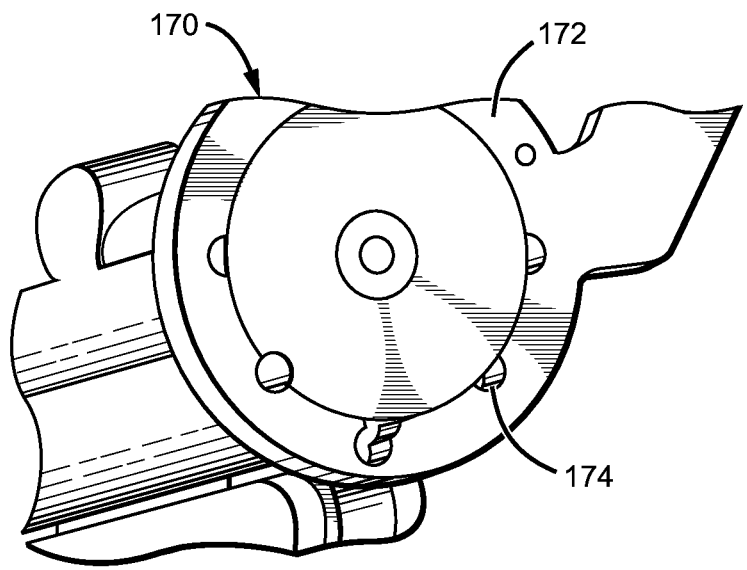

The present tensioning system is preferably arranged such that the rear section 102 of the reaction frame can rotate about first axis 106 while coupled to the forward section 100 of the reaction frame, such that the linear tension mechanism can be actuated by hand-operated lever 150 regardless of its angular position with respect to the first axis. This is accomplished with the use of a rear section/forward section rotation joint 170, best seen in FIG. 12a and in FIGS. 13a, 13d and 13e discussed below.

The present embodiment also preferably includes a rotation lock mechanism arranged to enable a user to lock hand-operated lever 150 in any of a plurality of predetermined rotation positions. This mechanism is illustrated in the isolated and cutaway views shown in FIGS. 13a-13e. The rotation lock mechanism preferably comprises a circular member 172 affixed to the proximal end of the forward section portion of rotation joint 170 and which includes cavities 174 located about the first axis at predetermined positions, and a shaft 176 which runs through the rear section 102 of the reaction frame parallel to first axis 106 and extends through circular member 172. Shaft 176 includes a locking knob 178 at its distal end which is larger than the shaft.

Figure 13E:
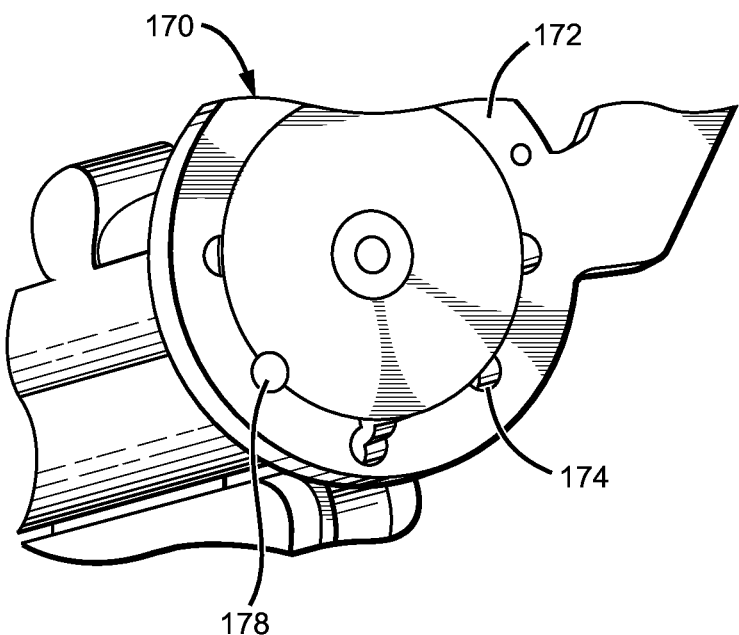

The rotation lock mechanism is arranged such that, when the shaft 176 is positioned such that locking knob 178 is clear of cavities 174, the hand-operated lever 150 can rotate about first axis 106 while coupled to the forward section 100 of the reaction frame. However, when the shaft is positioned such that locking knob 178 is in one of the cavities - as shown in FIG. 13e, the hand-operated lever is prevented from rotating.

A thumb button 180 is preferably located at the proximal end of shaft 176. The rotation lock mechanism is preferably arranged such that locking knob 178 is clear of cavities 174 when the thumb button is depressed, and the locking knob is pulled into one of the cavities by a spring mechanism (not shown) when the locking knob is aligned with one of the cavities and the thumb button is released.

Figure 14:
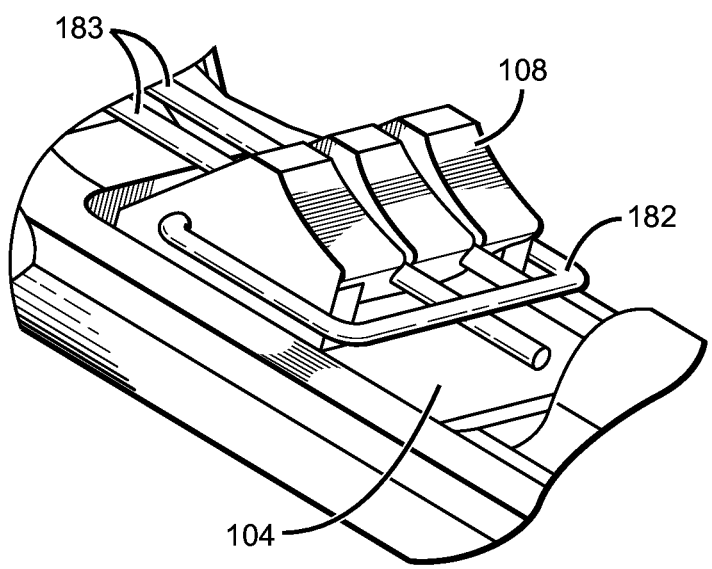
FIG. 14 is a perspective view of a spring-loaded wireform as might be used with a clam-type cleat used with the present surgical cable tensioning system.

As shown in FIG. 14, the present tensioning system might also include at least one spring-loaded wireform 182. The wireform can be flipped between 'up' and 'down' positions such that, when in its down position, it straddles clam-type cleat 108 and operates to urge any cables 183 within the grooves of the cleat further into the grooves. Other wireform orientations are also contemplated; one possible alternative arrangement is shown in FIG. 15, in which two wireforms 184 are flipped sideways with respect to cleat 182 in order to apply downward force to any cables within the cleat's grooves.

Figure 15:
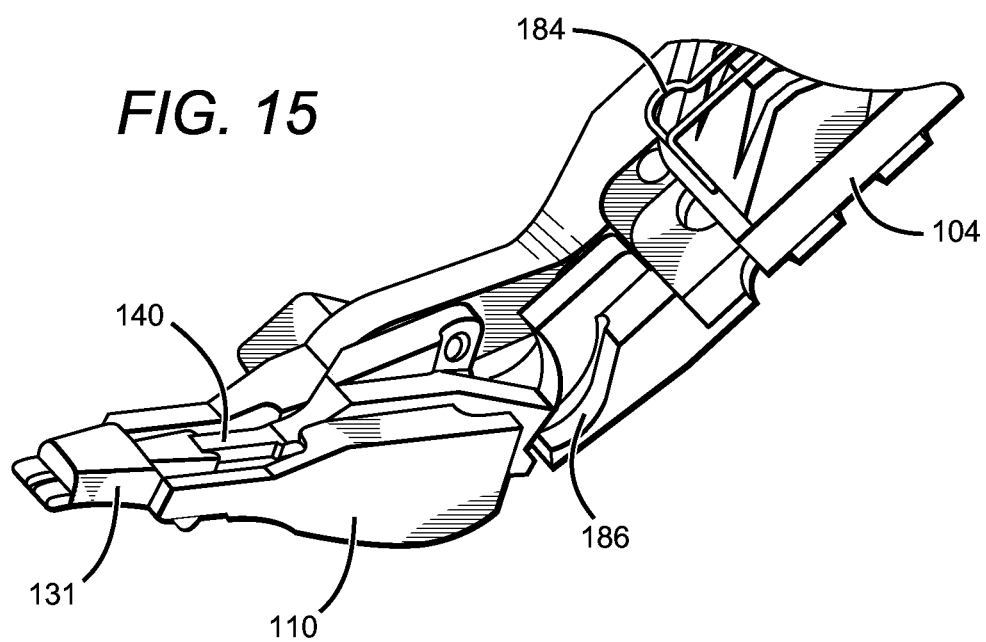
FIG. 15 is a perspective view of a 'scoop' feature as might be used with a TAD such as that shown in FIG. 8.

Another possible feature that might be included with the present tensioning system is shown in FIG. 15. Here, the TAD 110 includes a 'scoop' feature 186, which is arranged to conduct the cable as it exits the rear of the TAD and direct it toward cleat 108. For example, if the distal end of the TAD is tilted up and the cable is pushed through it, scoop 186 will deflect the end of the cable up towards the cleat.

The embodiment described above and shown in FIGS. 7a-15 allows a user to rotate the hand-operated lever and tilt the TAD as needed. This enables the user to get the optimal approach for tightening the cable. This capability can be important, because the insertion of the tensioning system can be quite limited by anatomy and the position of the patient on the operating table. As the surgeon (or assistant) typically have limited mobility while operating, this adjustability will be a very beneficial.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

We claim:

1. A surgical cable tensioning system, comprising:
a reaction frame;
a sliding platform within said reaction frame, said platform arranged to move linearly within said frame along a first axis;
a clam-type cleat attached to said sliding platform, said clam-type cleat comprising:
one or more grooves, each of which comprises two arrays of opposing ridges that converge to form a V-shape, each of said V-shaped grooves having a longitudinal axis which is approximately parallel to said first axis and adapted to receive a length of cable such that said received length of cable lies along an axis approximately parallel to said groove's longitudinal axis,
the ridges of each groove tilted relative to an axis perpendicular to said groove's longitudinal axis such that said length of cable is progressively captured between the ridges of said opposing arrays as it settles toward the bottom of said V-shaped groove when moved in a first direction relative to said cleat, and such that said length of cable is disengaged from said cleat by relaxing the axial force on the length of cable and moving the length of cable in the direction opposite said first direction;
a threading assist device (TAD), comprising:
at least one channel, each channel having a longitudinal axis which is approximately parallel to said first axis and adapted to receive a length of cable; and
a wrist joint which couples said TAD to the distal end of said reaction frame such that the distal end of said TAD can pivot up and down around a wrist joint axis which is perpendicular to said first axis; and
a linear tension mechanism coupled to said sliding platform and arranged to pull said sliding platform toward the proximal end of said reaction frame when actuated.

2. The system of claim 1, wherein said cleat comprises two of said grooves.

3. The system of claim 1, wherein said wrist joint is arranged such that said TAD has a range of motion of +90° to −60° with respect to said first axis.

4. The system of claim 1, wherein said wrist joint is arranged such that said TAD has a range of motion of +60° to −45° with respect to said first axis.

5. The system of claim 1, further comprising an angle lock mechanism arranged to enable a user to lock said TAD at one of a plurality of predetermined angles with respect to said first axis when actuated.

6. The system of claim 1, further comprising a set-bar mechanism arranged to engage with a cable retaining device through which one or more surgical cables is threaded en route to said TAD, and to cause said cable retaining device to lock said cables in place when said set-bar mechanism is actuated.

7. The system of claim 6, wherein said cable retaining device includes a device body and a locking wedge which locks said cables in place when forced into said device body, said set-bar mechanism arranged to apply force to said locking wedge when actuated.

8. The system of claim 7, said set-bar mechanism comprising:
a linear actuator within said TAD which engages with said locking wedge when actuated;
a hand-operated lever mounted to said reaction frame;
a shaft which is moved along an axis parallel to said first axis when said hand-operated lever is operated; and
a coupling means which operates to actuate said linear actuator when said hand-operated lever is operated.

9. The system of claim 8, wherein said coupling means comprises:
- a wheel which rotates about said wrist joint axis and is arranged to actuate said linear actuator when rotated;
- a pinion gear coupled to and concentric with said wheel; and
- a rack gear on the distal end of said set-bar mechanism shaft;
- said set-bar mechanism arranged such that said rack gear drives said pinion gear and said wheel to actuate said linear actuator when said hand-operated lever is operated, without impinging the rotation of said wrist joint.

10. The system of claim 1, wherein said reaction frame has forward and rear sections, said sliding platform positioned within said forward section.

11. The system of claim 10, wherein said linear tension mechanism comprises:
- a hand-operated lever mounted to the rear section of said reaction frame; and
- a tensioning mechanism coupled between said hand-operated lever and said sliding platform such that said sliding platform is pulled toward the rear section of said reaction frame when said hand-operated lever is actuated.

12. The system of claim 11, further comprising a rear section/forward section rotation joint which enables the rear section of said reaction frame to rotate about said first axis while coupled to the forward section of said reaction frame, such that said linear actuation mechanism can be actuated by said hand-operated lever regardless of its angular position with respect to said first axis.

13. The system of claim 12, further comprising a rotation lock mechanism arranged to enable a user to lock said hand-operated lever in any of a plurality of predetermined rotation positions.

14. The system of claim 13, wherein said rotation lock mechanism comprises:
- a circular member affixed to the proximal end of said forward section of said rotation joint and which includes cavities located about said first axis at predetermined positions; and
- a shaft which runs through said rear section of said reaction frame parallel to said first axis and extends through said circular member, said shaft including a locking knob at its distal end which is larger than said shaft;
- said rotation lock mechanism arranged such that, when said shaft is positioned such that said locking knob is clear of said cavities, said hand-operated lever can rotate about said first axis while coupled to the forward section of said reaction frame, and when said shaft is positioned such that said locking knob is in one of said cavities, said hand-operated lever is prevented from rotating about said first axis.

15. The system of claim 14, further comprising:
- a thumb button at the proximal end of said shaft; and
- a spring mechanism, said rotation lock mechanism arranged such that said locking knob is clear of said cavities when said thumb button is depressed, and said locking knob is pulled into one of said cavities by said spring mechanism when said locking knob is aligned with one of said cavities and said thumb button is released.

16. The system of claim 11, wherein said linear tension mechanism further comprises:
- a rod having a longitudinal axis which is oriented parallel to said first axis, said linear tension mechanism arranged such that said rod is moved along its longitudinal axis toward the proximal end of said reaction frame when said hand-operated lever is actuated; and
- a drawbar which is coupled to said sliding platform and extends through said rod, said drawbar having a feature which has a wider diameter than the rest of said drawbar near its proximal end;
- said rod and said drawbar arranged such that, when said hand-operated lever is actuated, the movement of said rod toward the proximal end of said reaction frame is coupled to the wider diameter portion of said drawbar and thereby causes said drawbar and thereby said sliding platform to be pulled toward the proximal end of said reaction frame.

17. The system of claim 16, wherein said tensioning mechanism comprises:
- a non-toothed ratchet mechanism coupled between said hand-operated lever and said rod which causes said rod to move toward the proximal end of said reaction frame when said hand-operated lever is actuated; and
- a keeper mechanism having 'normal' and 'release' states, said keeper mechanism operating to prevent said rod from moving back toward the distal end of said reaction frame when in its normal state, and allowing said rod to move back toward the distal end of said reaction frame when in its release state.

18. The system of claim 17, wherein said keeper mechanism includes a finger release positioned within reach of a user's finger when said user's hand is on said hand-operated lever, said keeper mechanism arranged to transition from its normal state to its release state when said finger release is pulled.

19. The system of claim 16, further comprising a stack of spring washers placed between the proximal end of said rod and the wider diameter portion of said drawbar such that the movement of said rod toward the proximal end of said reaction frame is coupled to the wider diameter portion of said drawbar by said spring washers.

20. The system of claim 1, further comprising at least one spring-loaded wireform which can be flipped between 'up' and 'down' positions, said at least one spring-loaded wireform arranged such that, when in said down position, it operates to urge any cables within the grooves of said clam-type cleat further into said grooves.

21. The system of claim 1, wherein said cable is polymer surgical cable.

22. The system of claim 1, wherein the angle formed by the arrays of opposing ridges is wider near the opening of each V-shaped groove than it is near the bottom of each V-shaped groove.

23. The system of claim 1, wherein each of said V-shaped grooves is arranged such that cables having a range of diameters can be captured by said groove without adjustment.

24. The system of claim 1, wherein the angle formed by the arrays of opposing ridges near the bottom of each V-shaped groove is ≤25°.

25. The system of claim 1, wherein the angle with which the ridges of each groove are tilted relative to an axis perpendicular to said groove's longitudinal axis is 45±20°.

* * * * *